United States Patent [19]

Chen et al.

[11] Patent Number: 5,314,920
[45] Date of Patent: May 24, 1994

[54] ETHYNYL-ALANINE ARYL/ALKYLSULFONYL-TERMINATED AMINO-DIOL COMPOUNDS FOR TREATMENT OF HYPERTENSION

[75] Inventors: Barbara B. Chen, Glenview; Gunnar J. Hanson, Skokie; John S. Baran, Winnetka, all of Ill.

[73] Assignee: G. D. Searle & Co., Chicago, Ill.

[21] Appl. No.: 916,447

[22] Filed: Jul. 20, 1992

[51] Int. Cl.$^5$ .............................................. A61K 31/16
[52] U.S. Cl. ..................................... 514/616; 564/154
[58] Field of Search ............... 564/154, 155, 157, 158, 564/159; 514/616

[56] References Cited

U.S. PATENT DOCUMENTS

| | | | |
|---|---|---|---|
| 4,619,944 | 10/1986 | Youssefyeh et al. | 514/513 |
| 4,902,706 | 2/1990 | Hanson et al. | 514/400 |
| 4,914,129 | 4/1990 | Bühlmayer et al. | 514/616 |
| 5,032,577 | 7/1991 | Fung et al. | 514/18 |

FOREIGN PATENT DOCUMENTS

| | | | |
|---|---|---|---|
| 30797/89 | 9/1989 | Australia | A61K 37/00 |
| 128762 | 12/1984 | European Pat. Off. | C07C 103/52 |
| 181110 | 5/1986 | European Pat. Off. | C07K 5/06 |
| 186977 | 7/1986 | European Pat. Off. | C07C 103/76 |
| 189203 | 7/1986 | European Pat. Off. | C07K 5/00 |
| 200406 | 12/1986 | European Pat. Off. | C07D 233/64 |
| 216539 | 4/1987 | European Pat. Off. | C07D 295/18 |
| 229667 | 7/1987 | European Pat. Off. | C07K 5/06 |
| 300189 | 1/1989 | European Pat. Off. | C07D 233/64 |
| 0353211 | 1/1990 | European Pat. Off. | |
| 416373 | 3/1991 | European Pat. Off. | C07D 233/64 |
| 87/04349 | 7/1987 | PCT Int'l Appl. | A61K 37/43 |

OTHER PUBLICATIONS

Umezawa et al., in *J. Antibiot.* (Tokyo), 23, 259–262 (1970).
Gross et al., *Science*, 175, 656 (1971).
Boger et al., *Nature*, 303, 81 (1983).
Kokubu et al., *Biochm. Biophys. Res. Commun.*, 118, 929 (1984).
Castro et al., *FEBS Lett.*, 167, 273 (1984).
Hanson et al., *Biochm. Biophys. Res. Commun.*, 132, 155–161 (1985); 146, 959–963 (1987).

*Primary Examiner*—Allen J. Robinson
*Assistant Examiner*—Brian M. Burn
*Attorney, Agent, or Firm*—J. Timothy Keane

[57] ABSTRACT

Compounds characterized generally as ethynyl alanine aryl/alkylsulfonyl-terminated amino diol derivatives are useful as renin inhibitors for the treatment of hypertension. Compounds of particular interest are those of the formula wherein $R^1$ is selected from isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaphthylmethyl and chloronaphthylmethyl; wherein $R^2$ is selected from hydrido, methyl, ethyl and phenyl; wherein $R^3$ is selected from hydrido, cyclohexylmethyl, benzyl, fluorobenzyl, chlorobenzyl, fluoronaphthylmethyl and chloronaphthylmethyl; wherein $R^5$ is propargyl or a propargyl-containing moiety; wherein $R^7$ is cyclohexylmethyl; and wherein $R^8$ is selected from n-propyl, isobutyl, cyclopropyl, cyclopropylmethyl, allyl and vinyl.

25 Claims, No Drawings

ETHYNYL-ALANINE ARYL/ALKYLSULFONYL-TERMINATED AMINO-DIOL COMPOUNDS FOR TREATMENT OF HYPERTENSION

FIELD OF THE INVENTION

Renin-inhibiting compounds are known for control of hypertension. Of particular interest herein are compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin I to produce the octapeptide known as angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al, in *J. Antibiot.* (Tokyo), 23, 259–262 (1970)]. This peptide, known as pepstatin, was found to reduce blood pressure in vivo after the injection of hog renin into nephrectomized rats [Gross et al, *Science*, 175, 656 (1971)]. Pepstatin has the disadvantages of low solubility and of inhibiting acid proteases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger et al, *Nature*, 303, 81 (1983)]. High molecular weight peptides are generally considered undesirable as drugs because gastrointestinal absorption is impaired and plasma stability is compromised.

Short peptide aldehydes have been reported as renin inhibitors [Kokubu et al, *Biochim. Biophys. Res. Commun.*, 118, 929 (1984); Castro et al, *FEBS Lett.*, 167, 273 (1984)]. Such compounds have a reactive C-terminal aldehyde group and would likely be unstable in vivo.

Other peptidyl compounds have been described as renin inhibitors. EP Appl. #128,762, published Dec. 18, 1984, describes dipeptide and tripeptide glyco-containing compounds as renin inhibitors [also see Hanson et al, *Biochm. Biophys. Res. Comm.*, 132, 155–161 (1985), 146, 959–963 (1987)]. EP Appl. #181,110, published May 14, 1986, describes dipeptide histidine derivatives as renin inhibitors. EP Appl. #186,977 published Jul. 9, 1986 describes renin-inhibiting compounds containing an alkynyl moiety, specifically a propargyl glycine moiety, attached to the main chain between the N-terminus and the C-terminus, such as N-[4(S)-[(N)-[bis(1-naphthylmethyl)acetyl]-DL-propargylglycylamino]-3(S)-hydroxy-6-methylheptanoyl]-L-isoleucinol. EP Appl. #189,203, published Jul. 30, 1986, describes peptidyl-aminodiols as renin inhibitors. EP Appl. #200,406, published Dec. 10, 1986, describes alkylnaphthylmethylpropionyl-histidyl aminohydroxy alkanoates as renin inhibitors. EP Appl. #216,539, published Apr. 1, 1987, describes alkylnaphthylmethylpropionyl aminoacyl aminoalkanoate compounds as renin inhibitors orally administered for treatment of renin-associated hypertension. PCT Application No. WO 87/04349, published Jul. 30, 1987, describes aminocarbonyl aminoacyl hydroxyether derivatives having an alkylamino-containing terminal substituent and which are described as having renin-inhibiting activity for use in treating hypertension. EP Appl. #300,189 published Jan. 25, 1989 describes amino acid monohydric derivatives having an alkylamino-alkylamino N-terminus and a β-alanine-histidine or sarcosyl-histidine attached to the main chain between the N-terminus and the C-terminus, which derivatives are mentioned as useful in treating hypertension. U.S. Pat. No. 4,902,706 which issued Feb. 13, 1990 describes a series of histidineamide-containing amino alkylaminocarbonyl-H-terminal aminodiol derivatives for use as renin inhibitors. U.S. Pat. No. 5,032,577 which issued Jul. 16, 1991 describes a series of histidineamide-aminodiol-containing renin inhibitors.

Several classes of sulfonyl-containing amino-diol renin-inhibitor compounds are known. For example, EP #229,667 published Jul. 22, 1987 describes generally alkylsulfonyl histidineamide amino diol C-terminated-alkyl compounds as renin inhibitors. Australian Patent Application #30797/89 published Sep. 7, 1989 describes alkylsulfonyl histineamide amino diol C-terminated-alkyl compounds as renin inhibitors, such as (S)-α-[(S)-α-[(t-butylsulphonyl)methyl]hydrocinnamamido]-N-[(1S,2R,3RS)-1-(cyclohexylmethyl)-2,3-dihydroxy-4,4-dimethylpentyl]imidazole-4-propionamide and (S)-α-[(S)-α-[(t-butylsulphonyl)methyl]hydrocinnamamido]-N-[(1S,2R,3S,4RS)-1-(cyclohexylmethyl)-2,3-dihydroxy-4-methylhexyl]imidazole-4-propionamide. U.S. Pat. No. 4,914,129 issued Apr. 3, 1990 describes sulfone-containing amino-hydroxyvaleryl compounds for use as antihypertensive agents, such as the compounds N-[2(S)-benzyl-3-tert-methylsulfonylpropionyl]-His-Cha-Val-n-butylamide and N-[2(R)-benzyl-3-tert-methylsulfonylpropionyl]-His-Cha-Val-n-butylamide. EP #416,373 published Mar. 13, 1991 describes alkylsulfonyl histidineamide amino diol compounds as renin-inhibitors, such as (S)-α-[(S)-α-[(tert-butylsulfonyl)methyl]-hydrocinnamamido]-N-[(1S,2R,3S)-1-(cyclohexylmethyl)-3-cyclopropyl-2,3-dihydroxypropyl]-imidazol-4-propionamide and (S)-α-[(S)-α-[(tert-butylsulfonyl)methyl]-hydrocinnamamido]-N-[(1S,2R,3R/S)-1-(cyclohexylmethyl)-3-cyclopropyl-2,3-dihydroxybutyl]imidazol-4-propionamide.

Propargyl-containing amino diol compounds for treatment of hypertension are described in U.S. application Ser. No. 07/783,955 of G. J. Hanson et al filed on Oct. 29, 1991.

DESCRIPTION OF THE INVENTION

Ethynyl alanine aryl/alkylsulfonyl-terminated amino diol compounds, having utility as renin inhibitors for treatment of hypertension in a subject, constitute a family of compounds of general Formula I:

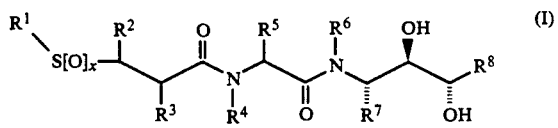 (I)

wherein R¹ is a group selected from alkyl, trifluoromethyl, cycloalkyl, cycloalkylalkyl, aryl, haloaryl, aralkyl and haloaralkyl; wherein x is a number selected from zero, one and two; wherein R² is selected from hydrido and alkyl; wherein R³ is a group selected from hydrido, cycloalkylalkyl, aralkyl and haloaralkyl; wherein each of R⁴ and R⁶ is a group independently selected from hydrido and methyl; wherein R⁵ is a propargyl moiety or a propargyl-containing moiety selected from

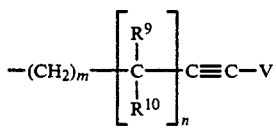

wherein V is selected from hydrido, alkyl, cycloalkyl, aryl and aralkyl; wherein each of R⁹ and R¹⁰ is a group independently selected from hydrido, alkyl, alkenyl, alkynyl, cycloalkyl and aryl; wherein m is a number selected from zero through three; wherein n is a number selected from zero through three; wherein R⁷ is a group selected from alkyl, cycloalkylalkyl and aralkyl; wherein R⁸ is a group selected from hydrido, alkyl, hydroxyalkyl, cycloalkyl, cycloalkylalkyl, alkenyl and haloalkenyl; and wherein any one of said R¹ through R¹⁰ groups having a substitutable position may be substituted with one or more groups selected from alkyl, hydroxy, alkoxy and alkenyl.

A preferred family of compounds consists of compounds of Formula I wherein R¹ is selected from alkyl, trifluoromethyl, cycloalkyl, cycloalkylalkyl, phenyl, halophenyl, phenylalkyl, halophenylalkyl, naphthyl, halonaphthyl, naphthylalkyl and halonaphthylalkyl; wherein x is a number selected from zero, one and two; wherein R² is selected from hydrido and alkyl; wherein R³ is selected from hydrido, cycloalkylalkyl, phenylalkyl, halophenylalkyl, naphthylalkyl and halonaphthylalkyl; wherein each of R⁴ and R⁶ is independently selected from hydrido and methyl; wherein R⁵ is propargyl moiety or a propargyl-containing moiety selected from

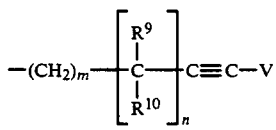

wherein V is selected from hydrido, alkyl, phenyl and benzyl; wherein each of R⁹ and R¹⁰ is independently selected from hydrido, alkyl, alkenyl, alkynyl, cycloalkyl and aryl; wherein m is a number selected from zero through three; wherein n is a number selected from zero through three; wherein R⁷ is selected from cyclohexylmethyl and benzyl, either one of which may be substituted with one or more groups selected from alkyl, hydroxy and alkoxy; and wherein R⁸ is selected from hydrido, alkyl, cycloalkyl, cycloalkylalkyl, hydroxyalkyl, alkenyl and haloalkenyl.

A more preferred family of compounds consists of compounds of Formula I wherein R¹ is selected from methyl, ethyl, n-propyl, isopropyl, n-butyl, isobutyl, sec-butyl, tert-butyl, trifluoromethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is a number selected from zero, one and two; wherein R² is selected from hydrido, methyl, ethyl and n-propyl; wherein R³ is selected from hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of R⁴ and R⁶ is independently selected from hydrido and methyl; wherein R⁵ is selected from

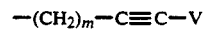

wherein V is selected from hydrido and alkyl; wherein m is a number selected from one through three; wherein R⁷ is cyclohexylmethyl; and wherein R⁸ is selected from methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl.

An even more preferred family of compounds consists of compounds Formula I wherein R¹ is selected from methyl, ethyl, n-propyl, isopropyl, benzyl, phenethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is zero or two; wherein R² is selected from hydrido, methyl, ethyl and n-propyl; wherein R³ is selected from hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of R⁴ and R⁶ is hydrido; wherein R⁵ is selected from

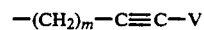

wherein V is selected from hydrido and methyl; wherein m is one or two; wherein R⁷ is cyclohexylmethyl; and wherein R⁸ is selected from ethyl, n-propyl, n-butyl, isobutyl, cyclopropyl, cyclobutyl, cyclopropylmethyl, allyl and vinyl.

A highly preferred family of compounds consists of compounds of Formula II

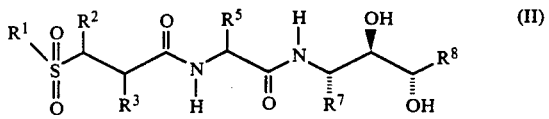 (II)

wherein R[1] is selected from isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaphthylmethyl and chloronaphthylmethyl; wherein R[2] is selected from hydrido, methyl, ethyl and phenyl; wherein R[3] is selected from hydrido, cyclohexylmethyl, benzyl, fluorobenzyl, chlorobenzyl, fluoronaphthylmethyl and chloronaphthylmethyl; wherein each of R[4] and R[6] is hydrido; wherein R[5] is selected from $$-(CH_2)_m-C\equiv C-V$$

wherein V is selected from hydrido and methyl; wherein m is one or two; wherein R[7] is cyclohexylmethyl; and wherein R[8] is selected from n-propyl, isobutyl, cyclopropyl, cyclopropylmethyl, allyl and vinyl.

The term "hydrido" denotes a single hydrogen atom (H). This hydrido group may be attached, for example, to an oxygen atom to form a hydroxyl group; or, as another example, one hydrido group may be attached to a carbon atom to form a

group; or, as another example, two hydrido groups may be attached to a carbon atom to form a —$CH_2$— group. Where the term "alkyl" is used, either alone or within other terms such as "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. Each of the terms sulfide, sulfinyl, and "sulfonyl", whether used alone or linked to other terms, denotes, respectively, the divalent radicals

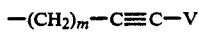

The term "alkenylalkyl" denotes a radical having a double-bond unsaturation site between two carbons, and which radical may consist of only two carbons or may be further substituted with alkyl groups which may optionally contain additional double-bond unsaturation. For any of the foregoing defined radicals, preferred radicals are those containing from one to about fifteen carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Also included in the family of compounds of Formula I are isomeric forms, including diastereoisomers.

Compounds of Formula I would be useful to inhibit enzymatic conversion of angiotensinogen to angiotensin I. When administered orally, a compound of Formula I would be expected to inhibit plasma renin activity and, consequently, lower blood pressure in a mammalian subject (e.g., a human subject). Thus, compounds of Formula I would be therapeutically useful in methods for treating hypertension by administering to a hypertensive subject a therapeutically-effective amount of a compound of Formula I. The phrase "hypertensive subject" means, in this context, a mammalian subject suffering from or afflicted by the effects of hypertension, or susceptible to a hypertensive condition if not treated to prevent or control such hypertension.

Description of the Synthetic Methods for the
Preparation of the Renin Inhibitors of the
Invention Synthetic Scheme 1

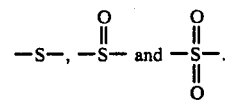

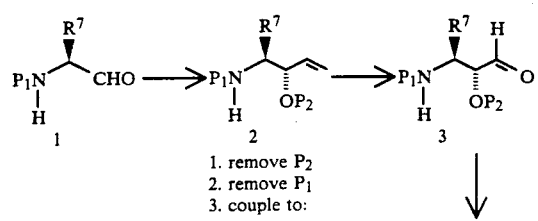

1. remove $P_2$
2. remove $P_1$
3. couple to:

Synthetic Scheme 1

-continued
Description of the Synthetic Methods for the
Preparation of the Renin Inhibitors of the
Invention

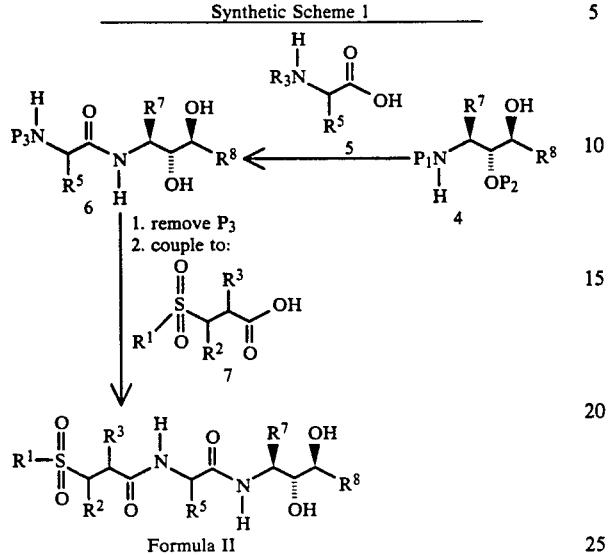

Formula II
wherein each of $R^1$, $R^2$, $R^3$, $R^5$, $R^7$ and $R^8$ are as defined above.

A suitably protected amino aldehyde 1 is treated with a Grignard reagent or other organometallic reagent, preferably vinylmagnesium bromide, to obtain the vinyl carbinol 2. This material, suitably protected, is oxidized, preferably with ozone, followed by dimethyl sulfide or zinc treatment, to give intermediate 3. The preceeding process is exemplified in Hanson, et al., J. Org. Chem. 50, 5399 (1985). This aldehyde is reacted with an organometallic reagent such as isobutylmagnesium chloride to give intermediate 4. Other suitable organometallic reagents include ethylmagnesium bromide, vinylmagnesium bromide, cyclopropylmagnesium bromide, and allylmagnesium bromide, but the choices are not limited to these reagents. After the formation of 4, further transformation of the added side chain is permitted, before going on the next depicted step. For example, the compound 4 derived from the addition of allylmagnesium bromide may be cyclopropanated via diazomethane and rhodium acetate, to give a cyclopropylmethyl side chain. Compound 4 is deprotected then coupled, using standard amide/peptide coupling methodology to protected triple bond-containing (ethynyl) amino acid derivatives 5 to give compound 6. These standard coupling procedures such as the carbodiimide, active ester (N-hydroxysuccinimide), and mixed carbonic anhydride methods are shown in Benoiton et al, *J. Org. Chem.*, 48, 2939 (1983) and Bodansky et al, "Peptide Synthesis", Wiley (1976). Ethynyl-containing amino acid derivatives may be prepared by using procedures such as found in Schollkopf, Tetrahedron 39, 2085 (1983). Intermediate 6 is then deprotected, then coupled to intermediate 7 using the standard amide/peptide coupling methodology, to give compounds of Formula II. Suitable protecting groups may be selected from among those reviewed by R. Geiger in "The Peptides", Academic Press, N.Y. vol. 2 (1979). For example, $P_1$ or $P_3$ may by Boc or Cbz; $P_2$ may be a typical oxygen protective group such as acetyl or t-butyldimethylsilyl.

Synthetic Scheme 2
Preparation of 7:

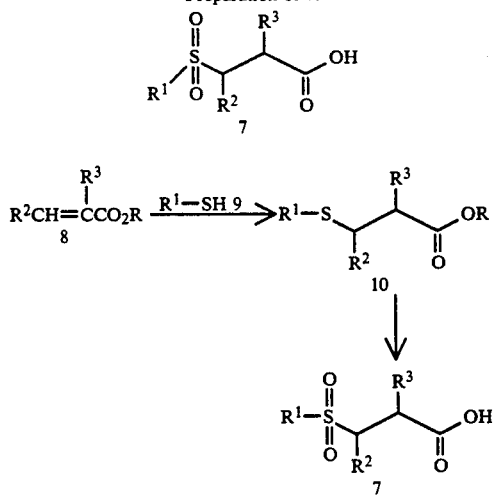

wherein $R^1$, $R^2$ and $R^3$ are as defined above
and R is lower alkyl.

Intermediate 7 may be prepared according to Synthetic Scheme 2. Michael addition of a suitable thiol 9 to a suitable acrylic acid 8 in the presence of base catalysts such as sodium hydride, triethyl amine or benzyltrimethylammonium hydroxide, afforded α, β di-substituted thio-propionic acid alkyl esters 10. In the case of $R^2$=H, a suitable malonic acid dialkyl ester is hydrolyzed to a mono ester, followed by concomitant decarboxylative dehydration to provide α substituted acrylic acid alkyl ester. Compound 10 is converted into its corresponding sulfone acid 7 via base hydrolysis, followed by oxidation with potassium peroxomonosulfate or perbenzoic acid.

Abbreviations: $P_1$ is an N-protecting group; $P_2$ is H or an oxygen protecting group; $P_3$ is an N-protecting group.

The following Steps 1–8 constitute specific exemplification of methods to prepare starting materials and intermediates embraced by the foregoing generic synthetic schemes. Those skilled in the art will readily understand that known variations of the conditions and processes of the following preparative procedures can be used to prepare the compounds of Steps 1–8. All temperatures expressed are in degrees Centigrade. Compounds of Examples 1–3 were prepared by using the procedures described in the following Steps 1–8:

Step 1: Preparation of (2R, 3S)-N-[(tert-Butyloxy)-carbonyl]-3-amino-2-acetoxy-4-phenylbutanal Ozone/oxygen was bubbled at −70° C. into a solution of (3S, 4S)-N-[(tert-Butyloxy)carbonyl]-4-amino-3-acetoxy-5-phenylpentene (2.55 g, 8.0 mmol) [prepared by the method of Hanson, et al., J. Org. Chem. 50, 5399 (1985)] in 100 mL of methylene chloride until a deep blue color persisted. Oxygen was introduced until the blue color completely faded, then 3.0 mL of Me₂S was added and the solution was allowed to warm to 0°–5° C. and stand overnight. The solvent was removed at 0° C. under vacuum yielding the title compound as a thick yellow oil which was used in the following step without purification.

Step 2: Preparation of (2S, 3R, 4S)-N-[(tert-Butyloxy)carbonyl]-2-amino-1-phenyl-3,4-dihydroxy-6-methylheptane The oil prepared in Step 1 was dissolved under nitrogen in 100 mL of dry THF and cooled to −70° C. To this solution was added 13 mL (26 mmol) of a 2.0M solution of isobutylmagnesium chloride in ether and the stirred mixture was allowed to warm to room temperature and stir for 2 hrs. After decomposition with MeOH/$H_2O$ the mixture was diluted with ether, washed with saturated $NH_4Cl$ solution twice, then dried and the solvents stripped off under vacuum. The residue was allowed to stand overnight in 80% MeOH-$H_2O$ containing excess ammonium hydroxide. The MeOH was stripped off and the mixture was extracted with ether. These extracts were combined, washed with water, dilute $KHSO_4$, then dried and evaporated to give 2.36 g of a yellow glass which crystallized from 50 mL of pentane on standing overnight. The yellow-white powder obtained was recrystallized from ether-hexane and furnished the title compound (0.41 g) as white, hairy needles, mp 134°–136° C., Rf (ether): single spot, 0.6. By chromatography of the mother liquors and crystallization of the appropriate fractions, an additional 0.22 g of product, mp 138°–139° C., was obtained. Anal: Calcd. for $C_{19}H_{31}NO_4$ (337.45): C, 67.62; H, 9.26; N, 4.15. Found: C, 67.51; H, 9.43; N, 4.24.

Step 3: Preparation of (2S, 3R, 4S)-N-[(tert-Butyloxy)carbonyl]-2-amino-1-cyclohexyl-3,4-dihydroxy-6-methylheptane The diol of Step 2, 0.27 g, was reduced in MeOH with 60 psi $H_2$ at 60° C. in 3 hrs using 5% Rh/C catalyst. After filtering, the solvent was stripped off and the white crystals were recrystallized from $CH_2Cl_2$-hexane to furnish tiny needles of the title compound, 0.19 g, mp 126°–128° C.; further recrystallization gave mp 128.5°–129.5° C. Rf (ether): single spot, 0.8. Anal: Calcd. for $C_{19}H_{37}NO_4$ (343.50): C, 66.43; H, 10.86, N, 4.08. Found: C, 66.43; H, 11.01; N, 4.03.

Step 4: Preparation of (2S,3R,4S) 2-amino-1-cyclohexyl-3,4-dihydroxy-6-methylheptane The title compound of Step 3 (10 g) was dissolved 6.9N HCl in dioxane (300 mL). the mixture was stirred for 30 minutes at room temperature. The solvent was removed in vacuo and to the residue was added 5% aqueous sodium hydroxide (30 mL) until a pH of 14 was obtained. This mixture was extracted with ether and the ether extract was washed with water and brine, then the solvent was evaporated to give the title compound (7.3 g, 100% yield). $^1H$ NMR: 300 MHz spectrum consistent with proposed structure. Anal: calcd. for $C_{14}H_{29}NO_2$: C, 69.07; H, 12.01; N, 5.78. Found: C, 69.19; H, 12.34; N, 5.78.

Step 5: Preparation of D,L Boc-C-propargylglycine

D,L C-propargylglycine (10 g) was suspended in tetrahydrofuran (30 mL). Water (30 mL), potassium carbonate (36.7 g), and di-tert-butyl-dicarbonate (21.9 g) were added. Additional water was added to produce a solution which was stirred for 12 hours at room temperature. The organic solvent was then evaporated and the aqueous solution was washed with ether, then acidified to pH 3 with 1N aqueous citric acid. The solution was extracted with methylene chloride and the solvent evaporated to give the title compound (18.9 g, 97% yield), used without further purification.

Step 6: Preparation of N-[1S,1R*-(cyclohexylmethyl)-2S*,3R*-dihydroxy-5-methylhexyl]-2-[[(1,1-dimethylethoxy)carbonyl]amino]-4-pentynamide D,L Boc-C-propargylglycine (1.2 g) was dissolved in methylene chloride (5 mL) and N-methyl piperidine (0.57 g) was added. The mixture was cooled to zero degrees centigrade and isobutyl chloroformate (0.78 g) was added. The mixture was stirred for 10 minutes whereupon the title compound of Step 4 (1.4 g) in methylene chloride (5 mL) was added and this mixture stirred for 15 minutes at 0° C. and 4° C. for 12 hours. The reaction mixture was washed successively with 1N citric acid, saturated sodium hydrogen carbonate, waster and brine. The organic layer was dried over magnesium sulfate and evaporated to dryness. $^1H$ NMR: 300 MHz spectrum consistent with proposed structure.

Step 7: Preparation of 2R*-amino-N-[1S,1R*-(cyclohexylmethyl)-2S*,3R*-dihydroxy-5-methylhexyl]-4-pentynamide The title compound of Step 6 (a 1:1 mixture of diastereomers) (0.76 g) was dissolved in a mixture of trifluoroacetic acid (4.9 mL) and methylene chloride (4.9 mL), and stirred for 30 minutes at room temperature. The solvent was then evaporated and the residue taken up in ethyl acetate. The organic layer was washed with saturated sodium hydrogen carbonate, water and brine, then dried over magnesium sulfate and evaporated. The residue was chromatographed on silica gel, eluting with ethanol-chloroform-ammonium hydroxide (15:85:0.5). The faster running of the two diastereomers was collected and evaporated to give the pure title compound (0.2 g, 34% yield). $^1H$ NMR: 300 MHz spectrum consistent with proposed structure. Anal: calcd. for $C_{19}H_{34}N_2O_3$: C, 67.4; H, 10.12; N, 8.31. Found: C, 66.6; H, 10.05; N, 8.02.

Step 8: Preparation of R,S-2-Benzyl-3-tert-butylsulphonyl-proionic acid

The title compound of Step 8 was prepared by procedures described in Step 8(a) to (d), below:

Step (a): Preparation of α-benzylacrylic acid ethyl ester:

A mixture of 8.5 g of KOH in 100 ml of ethanol was added at room temperature to 40 g of benzylmalonic acid diethyl ester in 80 ml of ethanol. The mixture was stirred overnight at room temperature, then concentrated by evaporation, thereafter 14 ml of water was added and then the mixture was acidified in an ice bath with 12.6 ml of concentrated hydrochloric acid. Partitioning between water and ether was carried out, the organic phase was dried and the ether was distilled off. Then, 26 ml of pyridine, 1.22 g of piperidine and 3.56 g of paraformaldehyde were added to the residue. The mixture was heated in an oil bath (130°) for 90 minutes, cooled, 440 ml of water was added and extraction was carried out 3 times with 150 ml of n-hexane. The combined organic phases were washed alternatively with water, 1N HCl, water, saturated $NaHCO_3$ solution and brine. The solution was dried ($MgSO_4$) and evaporated to give the title compound as colorless oil (26 g, 85% yield). $^1H$ NMR: 300 MHz spectrum consistent with proposed structure.

Step (b): Preparation of 2-benzyl-3-tert.-butylthiopropionic acid ethyl ester:

4.0 g of α-benzylacrylic acid ethyl ester of step (a) was dissolved in 40 ml of THF and reacted at room temperature with a mixture of 2.39 ml of tert.-butylmercaptan and 459 mg of sodium hydride dispersion (60% in oil). The mixture was stirred at room temperature for 5 hours, poured into 1N hydrochloric acid and extracted with ethyl acetate. The extracts were dried and concentrated by evaporation. The residue was purified by flash chromatography on silica gel, eluting with hexane-ethyl acetate (8:1). Colorless oil (4 g, 68% yield). ¹H NMR: 300 MHz spectrum consistent with proposed structure. Anal: calcd. for C₁₆H₂₄O₂S: C, 68.53; H, 8.63. Found: C, 68.10; H, 8.47.

Step (c): Preparation of 2-benzyl-3-tert.-butylthiopropionic acid:

400 mg of 2-benzyl-3-tert.-butylthio-propionic acid ethyl ester was dissolved in 1.5 ml of methanol and then reacted with 5 ml of 2N potassium hydroxide solution. The mixture was stirred at room temperature overnight and concentrated by evaporation. The residue was diluted with water and washed with ether. The aqueous layer was acidified to pH 3 with 2N HCl, and then evaporated to give the title compound (280 mg, 78% yield). ¹H NMR: 300 MHz spectrum consistent with proposed structure.

Step (d): Preparation of 2-benzyl-3-tert.-butylsulphonylpropionic acid:

280 mg of 2-benzyl-3-tert.-butylthio-propionic acid was dissolved in 5 ml of methanol and, while cooling with ice, 1 g of potassium peroxomonosulfate in 4 ml of water was added and the whole was stirred at room temperature overnight. The solution was diluted with water and extracted with methylene chloride, and the extracts were dried and concentrated by evaporation (260 mg, 82% yield). ¹H NMR: 300 MHz spectrum consistent with proposed structure. Anal. calcd. for C₁₄H₂₀O₄S: C, 59.13; H, 7.09. Found: C, 59.39; H, 7.08.

the following working Examples are provided to illustrate synthesis of Compounds 1–36 of the present invention and are not intended to limit the scope thereof. Those skilled in the art will readily understand that known variations of the conditions and processes of the following preparative procedures can be used to prepare the compounds of the Examples. All temperatures expressed are in degrees Centigrade.

EXAMPLE 1

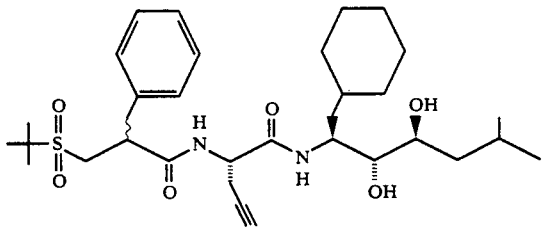

N-[[1R*-[[1S,1R*(cyclohexylmethyl)-2S*,3R*-dihydroxy-5-methylhexyl]amino]carbonyl]-3-butynyl]-α-[[(1,1-dimethylethyl)sulfonyl]methyl]benzenepropanamide The title compound of Step 8 (759 mg, 2.67 mmol) was dissolved at room temperature in a mixture of dimethylformamide (11 mL) and pyridine (2 mL) and to this solution was added N,N-disuccinimidyl carbonate (622 mg, 2.43 mmol) and 4-dimethylaminopyridine (30 mg). The mixture was stirred for 3 hours, and then the title amine of Step 7 (820 mg, 2.43 mmol) was added, followed by diisopropyl ethylamine (0.42 mL). This mixture was allowed to stir for 12 hours. The solvent was then evaporated and the residue dissolved in ethyl acetate (60 mL). The mixture was washed successively with water, 0.5M citric acid saturated sodium bicarbonate and brine, then dried over sodium sulfate and the solvent evaporated. The residue was purified by flash chromatography on silica gel and eluted with methanol-methylene chloride (2%) to give the title compound as white powder (900 mg, 56% yield). ¹H NMR: 300 MHz spectrum consistent with proposed structure. Anal: calcd. for C₃₃H₅₂N₂O₆S: C, 65.53; H, 8.66; N, 4.63. Found: C, 65.15; H, 8.74; N, 4.69.

EXAMPLE 2

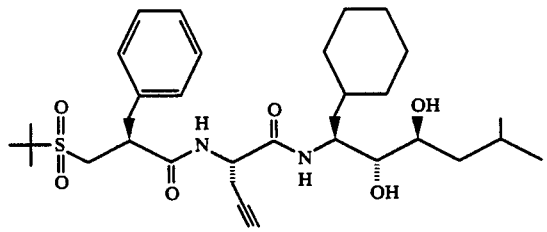

N-[[1R*-[[1S,1R*(cyclohexylmethyl)-2S*,3R*-dihydroxy-5-methylhexyl]amino]carbonyl]-3-butynyl]-αR*-[[(1,1-dimethylethyl)sulfonyl]methyl]benzenepropanamide 400 mg of crude material containing title compound of Example #1 was separated by chromatography on a 2 mm silica gel plate, eluting with CH₂Cl₂—CH₃OH (50:1). Two isomers were obtained: Isomer "A" (70 mg) had an Rf=0.7 and Isomer "B" (150 mg) had an Rf=0.6 on the t.l.c. plate, eluting with CH₂Cl₂—CH₃OH (10:1). The "B" isomer, characterized by the following analytical data, is identified as the compound of Example #2. Anal: calcd. for isomer B C₃₃H₅₂N₂O₆S+0.3 H₂O: C, 64.95; H, 8.69; N, 4.59. Found: C, 64.91; H, 8.69; N, 4.54.

EXAMPLE 3

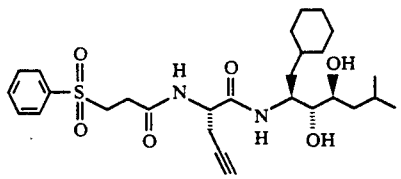

N-[1S,1R*(cyclohexylmethyl)-2S*,3R*-dihydroxy-5-methylhexyl]-2R*-[[1-oxo-3-[phenylsulfonyl]propyl]amino]-4-pentynamide 3-(Phenylsulfonyl) propionic acid (32 mg, 0.15 mmol) was dissolved in benzene (2 ml) at room temperature. To this, oxalyl chloride (19 mg, 0.15 mmol) and catalytic amount of dimethylformamide were added, and the mixture was allowed to stir for 2 hours. The solvent was then evaporated, and the residue was dissolved in methylene chloride (4 ml) and the title amine of Step 7 (50 mg, 0.15 mmol) was added, followed by 1-methylpiperidine (15 mg, 0.15 mmol). This mixture was allowed to stir for 16 hours. The solvent was then evaporated and the residue was dissolved in ethyl acetate (10 ml), and washed with water, 1N HCl, saturated sodium bicarbonate and brine, then dried (Na₂SO₄) and evaporated to give the title compound as a white powder (60 mg, 74% yield). ¹H NMR: 300 MHz spectrum consistent with proposed structure. Anal: calcd. for C₂₈H₄₂N₂O₆S: C, 62.90; H, 7.92, N, 5.24. Found: C, 63.00; H, 8.17, N, 5.16.

Compounds #4–36, as shown in Table I below, may be synthesized by reference to the foregoing specific and general procedures for preparing compounds of Formula I.

TABLE I

| Example Compound No. | Structure |
|---|---|
| 4 | 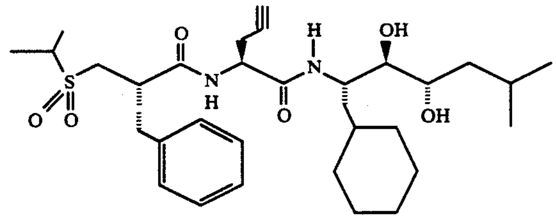 |
| 5 | 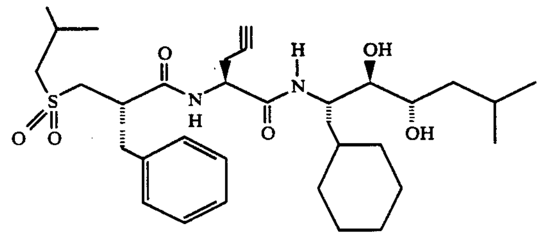 |
| 6 | 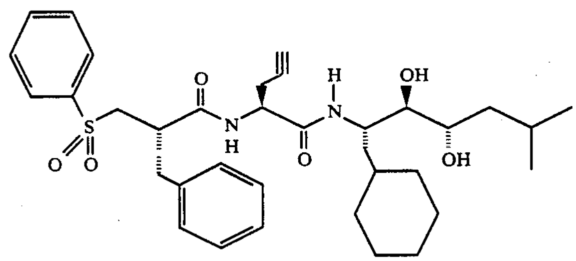 |
| 7 | 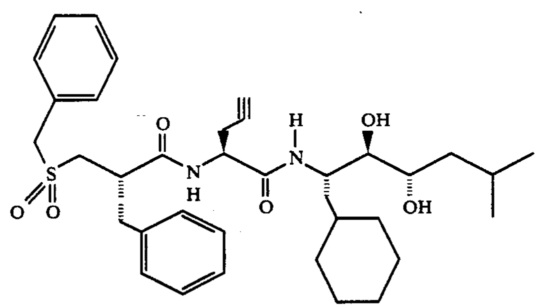 |
| 8 | 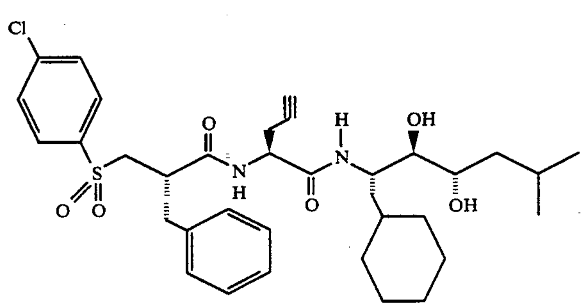 |

TABLE I-continued

| Example Compound No. | Structure |
| --- | --- |
| 9 | 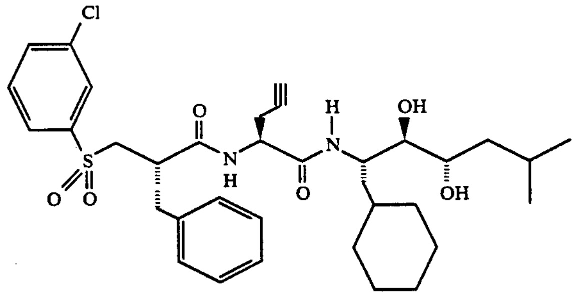 |
| 10 | 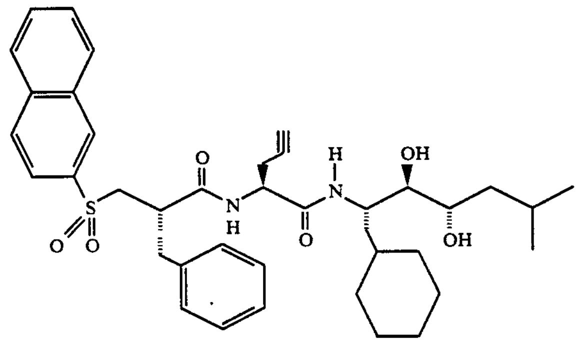 |
| 11 | 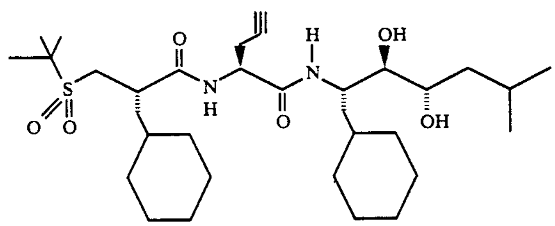 |
| 12 | 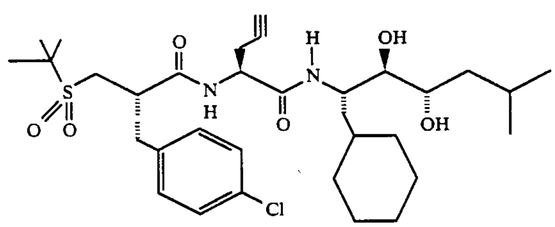 |
| 13 | 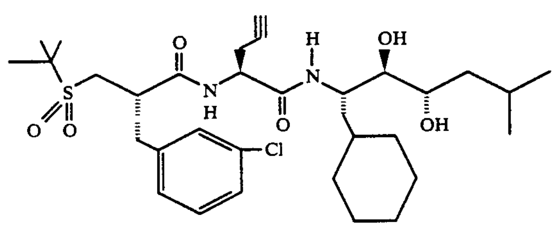 |
| 14 | 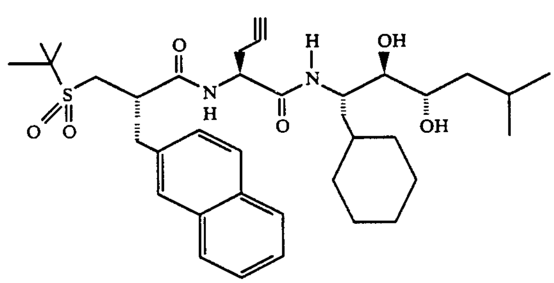 |

TABLE I-continued

| Example Compound No. | Structure |
| --- | --- |
| 15 | 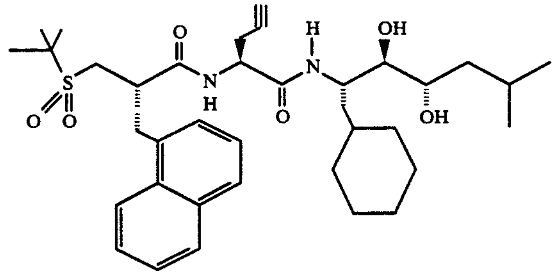 |
| 16 | 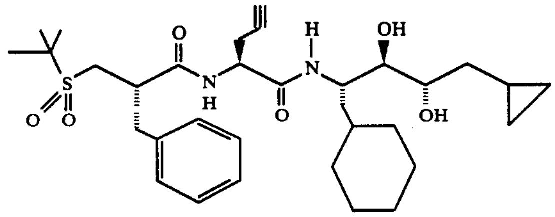 |
| 17 | 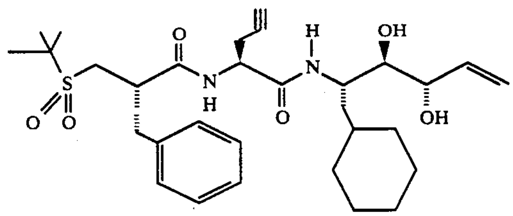 |
| 18 | 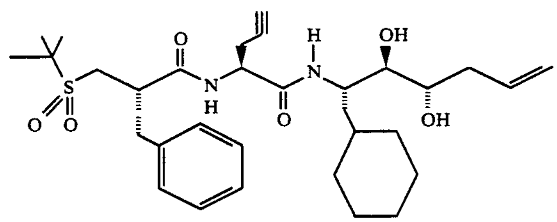 |
| 19 | 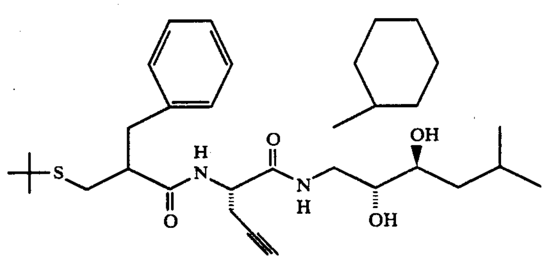 |
| 20 | 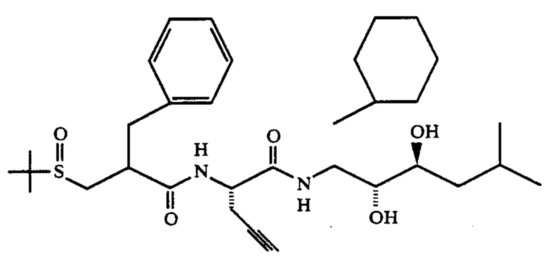 |

TABLE I-continued

| Example Compound No. | Structure |
|---|---|
| 21 | 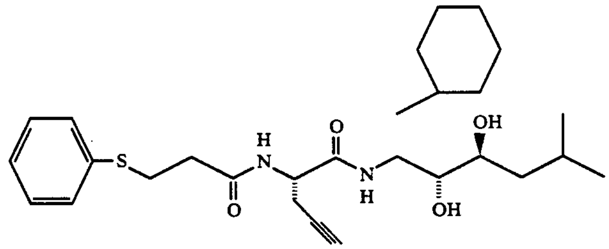 |
| 22 | 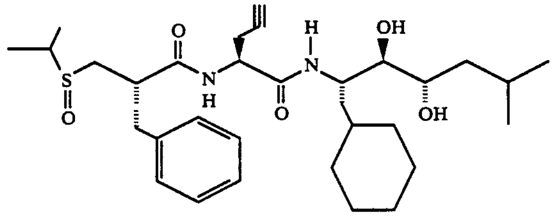 |
| 23 | 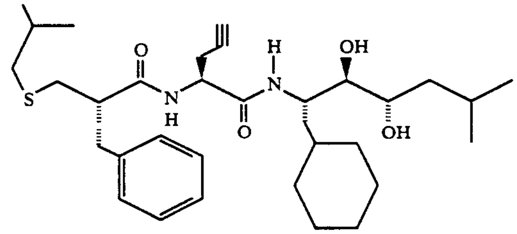 |
| 24 | 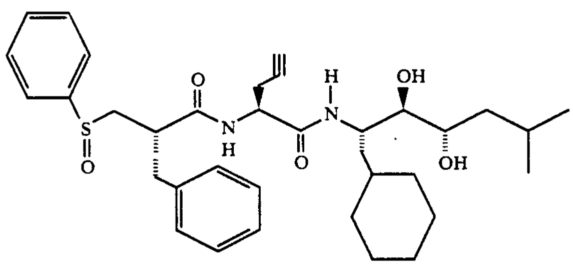 |
| 25 | 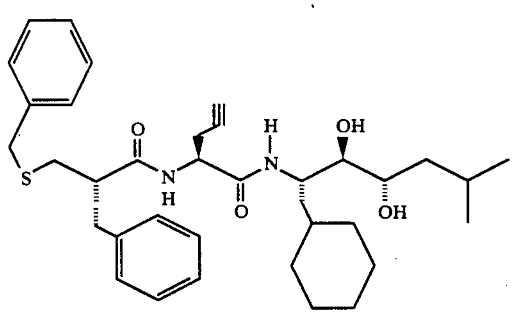 |
| 26 | 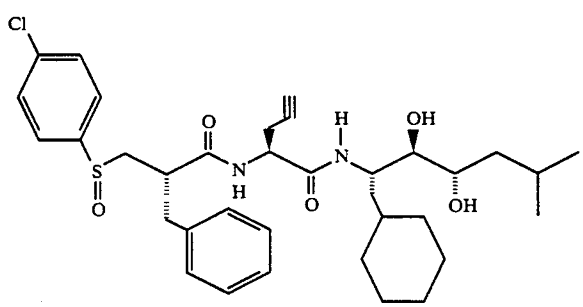 |

TABLE I-continued
| Example Compound No. | Structure |
| --- | --- |
| 27 | 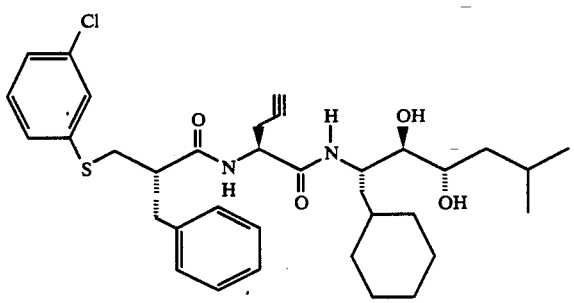 |
| 28 | 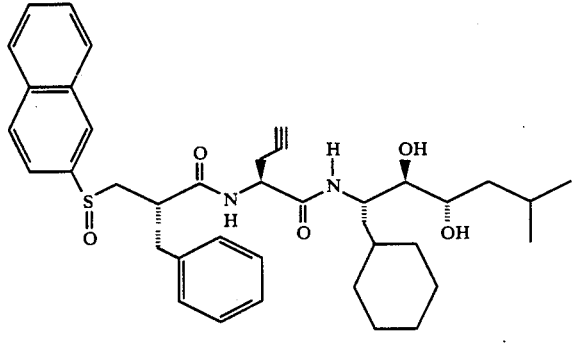 |
| 29 | 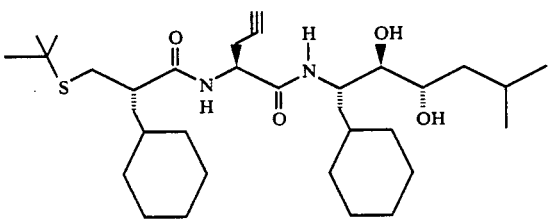 |
| 30 | 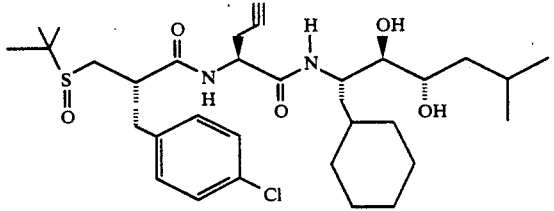 |
| 31 | 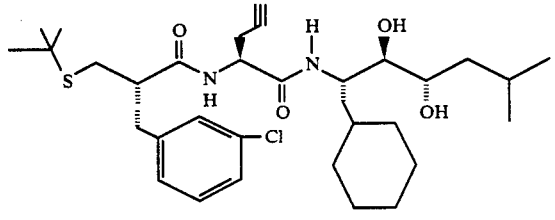 |

TABLE I-continued

| Example Compound No. | Structure |
|---|---|
| 32 | 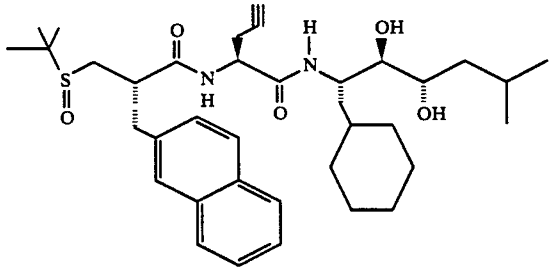 |
| 33 | 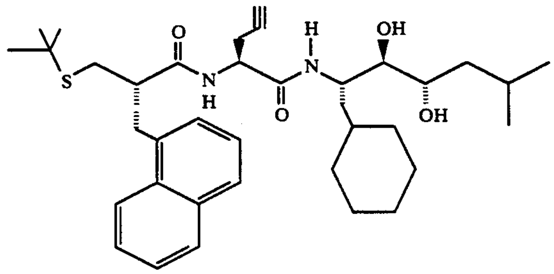 |
| 34 | 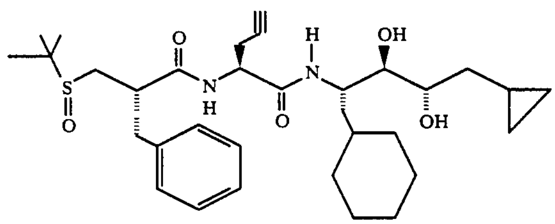 |
| 35 | 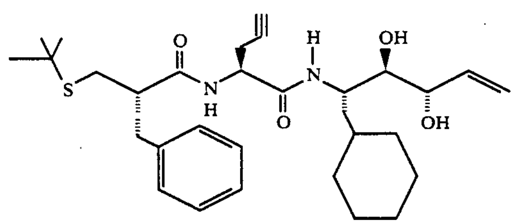 |
| 36 | 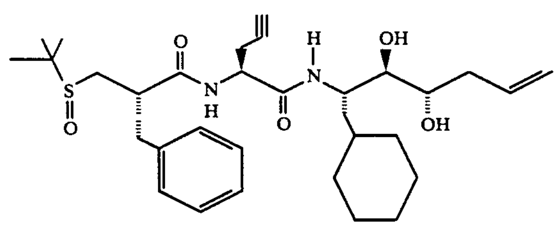 |

BIOLOGICAL EVALUATION

Human Renin Inhibition in vitro

Compounds of Formula I were evaluated as inhibitors of human renin in an vitro assay, as follows: This human renin inhibition test has been previously described in detail [Papaioannou et al., *Clinical and Experimental Hypertension*, A7 (9), 1243–1257 (1985)]. Human renin was obtained from the National Institute for Biological Standards, London. An incubation mixture was prepared containing the following components: in a total volume of 0.25 mL: 100 mM Tris-acetate buffer at pH 7.4, $25 \times 10^{-6}$ Goldblatt units of renin, 0.05 mL of plasma from human volunteers taking oral contraceptives, 6.0 mM Na-EDTA, 2.4 mM phenylmethyl sulfonyl fluoride, 1.5 mM 8-hydroxyquinoline, 0.4 mg/mL bovine serum albumin (BSA), and 0.024 mg/mL neomycin sulfate. This mixture was incubated for two hours at 37° C. in the presence or absence of renin inhibitors. The produced angiotensin I was determined by radioimmunoassay (New England Nuclear kit). Test compounds to be assayed were dissolved in DMSO and diluted with 100 mM Tris-acetate buffer at pH 7.4 containing 0.5% BSA to the appropriate concentration. The final concentration of organic solvent in the reaction mixture was less than 1%. Control incubations at 37° C. were used to correct for effects of organic solvent on renin activity.

The in vitro enzymatic conversion of angiotensinogen to angiotensin I was inhibited by test compounds of the invention as indicated in Table II, below:

TABLE II

| Human Renin in vitro Inhibition Data | |
|---|---|
| Compound Example # | IC$_{50}$ Human Renin (nM) |
| Example 1 | 0.23 |
| Example 2 | 0.17 |
| Example 3 | 34% inhibition @ 100 nM |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 400 mg of active compound per unit dosage form. A more preferred dosage will contain from about 2 mg to about 200 mg of active compound per unit dosage form. Most preferred is a dosage form containing from about 3 mg to about 100 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I:

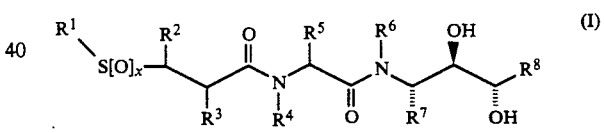

wherein $R^1$ is selected from the group consisting of alkyl, trifluoromethyl, cycloalkyl, cycloalkylalkyl, aryl, haloaryl, aralkyl and haloaralkyl; wherein x is a number selected from the group consisting of zero, one and two; wherein $R^2$ is selected from the group consisting of hydrido and alkyl; wherein $R^3$ is selected from the group consisting of hydrido, cycloalkylalkyl, aralkyl and haloaralkyl; wherein each of $R^4$ and $R^6$ is independently selected from the group consisting of hydrido and methyl; wherein $R^5$ is propargyl or a propargyl-containing moiety; wherein $R^7$ is selected from the group consisting of alkyl, cycloalkylalkyl and aralkyl; wherein $R^8$ is a group selected from the group consisting of hydrido, alkyl, hydroxyalkyl, cycloalkyl, cycloalkylalkyl, alkenyl and haloalkenyl; and wherein any one of said $R^1$ through $R^8$ groups having a substitutable position may be substituted with one or more groups selected from the group consisting of alkyl, hydroxy, alkoxy and alkenyl.

2. Compound of claim 1 wherein $R^1$ is selected from the group consisting of alkyl, trifluoromethyl, cycloalkyl, cycloalkylalkyl, phenyl, halophenyl, phenylalkyl, halophenylalkyl, naphthyl, halonaphthyl, naphthylalkyl and halonaphthylalkyl; wherein x is a number selected from the group consisting of zero, one and two; wherein R² is selected from the group consisting of hydrido and alkyl; wherein R³ is selected from the group consisting of hydrido, cycloalkylalkyl, phenylalkyl, halophenylalkyl, naphthylalkyl and halonaphthylalkyl; wherein each of R⁴ and R⁶ is independently selected from the group consisting of hydrido and methyl; wherein R⁵ is propargyl or a propargyl-containing moiety; wherein R⁷ is selected from the group consisting of cyclohexylmethyl and benzyl, either one of which may be substituted with one or more groups selected from the group consisting of alkyl, hydroxy and alkoxy; and wherein R⁸ is selected from the group consisting of hydrido, alkyl, cycloalkyl, cycloalkylalkyl, hydroxyalkyl, alkenyl and haloalkenyl.

3. Compound of claim 2 wherein R¹ is selected from the group consisting of methyl, ethyl, n-propyl, isopropyl, n-butyl, isobutyl, sec-butyl, tert-butyl, trifluoromethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is a number selected from the group consisting of zero, one and two; wherein R² is selected from hydrido, methyl, ethyl and n-propyl; wherein R³ is selected from hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of R⁴ and R⁶ is independently selected from the group consisting of hydrido and methyl; wherein R⁵ is propargyl or a propargyl-containing moiety; wherein R⁷ is cyclohexylmethyl; and wherein R⁸ is selected from the group consisting of methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl.

4. Compound of claim 3 wherein R¹ is selected from the group consisting of methyl, ethyl, n-propyl, isopropyl, benzyl, phenethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is zero or two; wherein R² is selected from the group consisting of hydrido, methyl, ethyl and n-propyl; wherein R³ is selected from the group consisting of hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of R⁴ and R⁶ is hydrido; wherein R⁵ is propargyl or a propargyl-containing moiety; wherein R⁷ is cyclohexylmethyl; and wherein R⁸ is selected from the group consisting of ethyl, n-propyl, n-butyl, isobutyl, cyclopropyl, cyclobutyl, cyclopropylmethyl, allyl and vinyl.

5. Compound of claim 4 of Formula II

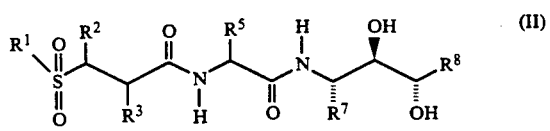

wherein R¹ is selected from the group consisting of isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaphthylmethyl and chloronaphthylmethyl; wherein R² is selected from the group consisting of hydrido, methyl, ethyl and phenyl; wherein R³ is selected from the group consisting of hydrido, cyclohexylmethyl, benzyl, fluorobenzyl, chlorobenzyl, fluoronaphthylmethyl and chloronaphthylmethyl; wherein each of R⁴ and R⁶ is hydrido; wherein R⁵ is propargyl or a propargyl-containing moiety; wherein R⁷ is cyclohexylmethyl; and wherein R⁸ is selected from the group consisting of n-propyl, isobutyl, cyclopropyl, cyclopropylmethyl, allyl and vinyl.

6. Compound of claim 5 selected from compounds, their tautomers, and the pharmaceutically-acceptable esters thereof, of the group consisting of

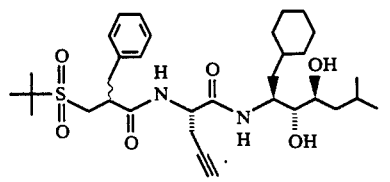

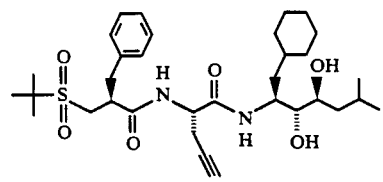

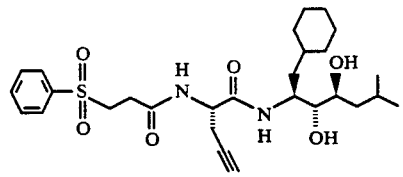

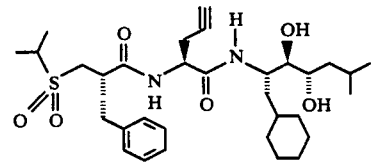

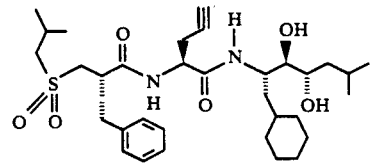

-continued

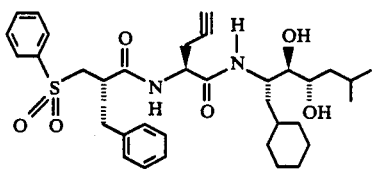
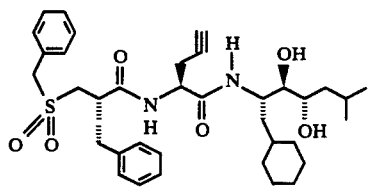
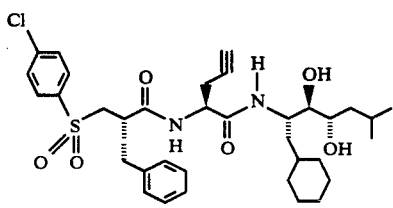
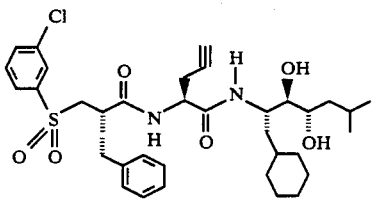
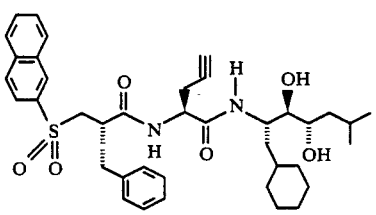
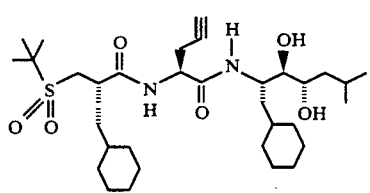
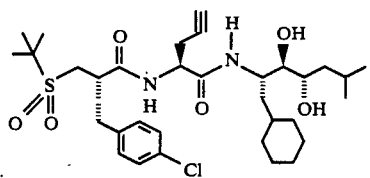
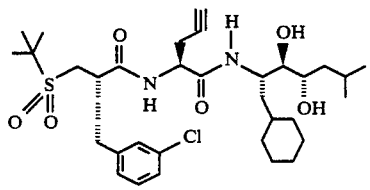

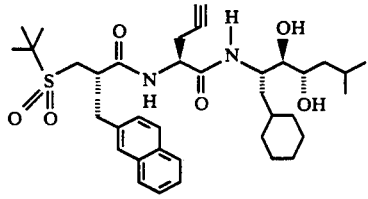
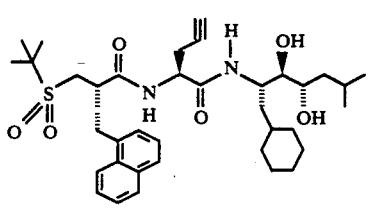
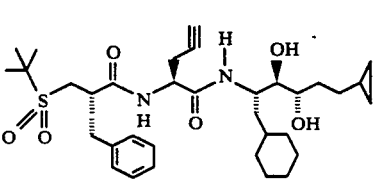
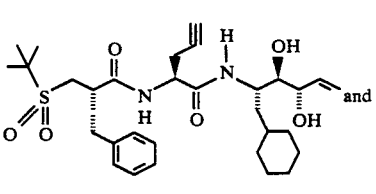
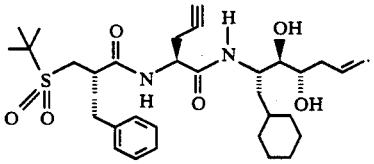

7. Compound of claim 6 which is N-[[1R*-[[1S,1R*(cyclohexylmethyl)-2S*,3R*-dihydroxy-5-methylhexyl]amino]carbonyl]-3-butynyl]-α-[[(1,1-dimethylethyl)sulfonyl]methyl]benzenepropanamide.

8. Compound of claim 6 which is N-[[1R*-[[1S,1R*-(cyclohexylmethyl)-2S*,3R*-dihydroxy-5-methylhexyl]amino]carbonyl]-3-butynyl]-αR*-[[(1,1-dimethylethyl)sulfonyl]methyl]benzenepropanamide.

9. Compound of claim 6 which is N-[[1S,1R*(cyclohexylmethyl)-2S*,3R*-dihydroxy-5-methylhexyl]-2R*-[[1-oxo-3-(phenylsulfonyl)propyl]amino]-4-pentynamide.

10. A pharmaceutical composition comprising a therapeutically-effective amount of a renin-inhibiting compound and a pharmaceutically-acceptable carrier or diluent, said renin-inhibiting compound selected from a family of compounds of Formula I:

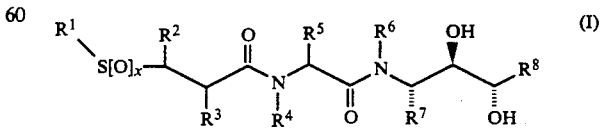

wherein $R^1$ is selected from the group consisting of alkyl, trifluoromethyl, cycloalkyl, cycloalkylalkyl, aryl, haloaryl, aralkyl and haloaralkyl; wherein x is a number selected from the group consisting of zero, one and two; wherein R² is selected from hydrido and alkyl; wherein R³ is selected from the group consisting of hydrido, cycloalkylalkyl, aralkyl and haloaralkyl; wherein each of R⁴ and R⁶ is independently selected from the group consisting of hydrido and methyl; wherein R⁵ is propargyl or a propargyl-containing moiety; wherein R⁷ is selected from the group consisting of alkyl, cycloalkylalkyl and aralkyl; wherein R⁸ is selected from the group consisting of hydrido, alkyl, hydroxyalkyl, cycloalkyl, cycloalkylalkyl, alkenyl and haloalkenyl; and wherein any one of said R¹ through R⁸ groups having a substitutable position may be substituted with one or more groups selected from alkyl, hydroxy, alkoxy and alkenyl.

11. The composition of claim 10 wherein R¹ is selected from the group consisting of alkyl, trifluoromethyl, cycloalkyl, cycloalkylalkyl, phenyl, halophenyl, phenylalkyl, halophenylalkyl, naphthyl, halonaphthyl, naphthylalkyl and halonaphthylalkyl; wherein x is a number selected from the group consisting of zero, one and two; wherein R² is selected from the group consisting of hydrido and alkyl; wherein R³ is selected from the group consisting of hydrido, cycloalkylalkyl, phenylalkyl, halophenylalkyl, naphthylalkyl and halonaphthylalkyl; wherein each of R⁴ and R⁶ is independently selected from the group consisting of hydrido and methyl; wherein R⁵ is propargyl or a propargyl-containing moiety; wherein R⁷ is selected from the group consisting of cyclohexylmethyl and benzyl, either one of which may be substituted with one or more groups selected from the group consisting of alkyl, hydroxy and alkoxy; and wherein R⁸ is selected from the group consisting of hydrido, alkyl, cycloalkyl, cycloalkylalkyl, hydroxyalkyl, alkenyl and haloalkenyl.

12. The composition of claim 11 wherein R¹ is selected from the group consisting of methyl, ethyl, n-propyl, isopropyl, n-butyl, isobutyl, sec-butyl, tert-butyl, trifluoromethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is a number selected from the group consisting of zero, one and two; wherein R² is selected from the group consisting of hydrido, methyl, ethyl and n-propyl; wherein R³ is selected from the group consisting of hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of R⁴ and R⁶ is independently selected from the group consisting of hydrido and methyl; wherein R⁵ is propargyl or a propargyl-containing moiety; wherein R⁷ is cyclohexylmethyl; and wherein R⁸ is selected from the group consisting of methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl.

13. The composition of claim 12 wherein R¹ is selected from the group consisting of methyl, ethyl, n-propyl, isopropyl, benzyl, phenethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylpropyl, naphthyl, fluoronaphthyl, chloronaphthyl, naphthylmethyl, naphthylethyl, fluoronaphthylmethyl and chloronaphthylmethyl; wherein x is zero or two; wherein R² is selected from the group consisting of hydrido, methyl, ethyl and n-propyl; wherein R³ is selected from the group consisting of hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of R⁴ and R⁶ is hydrido; wherein R⁵ is propargyl or a propargyl-containing moiety; wherein R⁷ is cyclohexylmethyl; and wherein R⁸ is selected from the group consisting of ethyl, n-propyl, n-butyl, isobutyl, cyclopropyl, cyclobutyl, cyclopropylmethyl, allyl and vinyl.

14. The composition of claim 13 wherein said renin-inhibiting compound is selected from compounds of Formula II

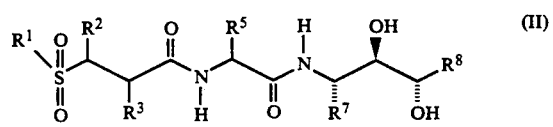

wherein R¹ is selected from the group consisting of isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaphthylmethyl and chloronaphthylmethyl; wherein R² is selected from the group consisting of hydrido, methyl, ethyl and phenyl; wherein R³ is selected from the group consisting of hydrido, cyclohexylmethyl, benzyl, fluorobenzyl, chlorobenzyl, fluoronaphthylmethyl and chloronaphthylmethyl; wherein each of R⁴ and R⁶ is hydrido; wherein R⁵ is propargyl or a propargyl-containing moiety; wherein R⁷ is cyclohexylmethyl; and wherein R⁸ is selected from the group consisting of n-propyl, isobutyl, cyclopropyl, cyclopropylmethyl, allyl and vinyl.

15. The composition of claim 14 wherein said renin-inhibiting compound is N-[[1R*-[[1S,1R*-(cyclohexylmethyl)-2S*,3R*-dihydroxy-5-methylhexyl]amino]carbonyl]-3-butynyl]-α-[[(1,1-dimethylethyl)sulfonyl]methyl]benzenepropanamide.

16. The composition of claim 14 wherein said renin-inhibiting compound is N-[[1R*-[[1S,1R*-(cyclohexylmethyl)-2S*,3R*-dihydroxy-5-methylhexyl]amino]carbonyl]-3-butynyl]-αR*-[[(1,1-dimethylethyl)sulfonyl]methyl]benzenepropanamide.

17. The composition of claim 14 wherein said renin-inhibiting compound is N-[[1S,1R*-(cyclohexylmethyl)-2S*,3R*-dihydroxy-5-methylhexyl]-2R*-[[1-oxo-3-(phenylsulfonyl)propyl]amino]-4-pentynamide.

18. A therapeutic method for treating hypertension, said method comprising administering to a hypertensive patient a therapeutically-effective amount of a compound of Formula I:

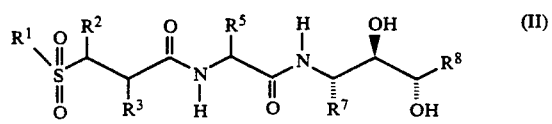

wherein R¹ is selected from the group consisting of alkyl, trifluoromethyl, cycloalkyl, cycloalkylalkyl, aryl, haloaryl, aralkyl and haloaralkyl; wherein x is a number selected from the group consisting of zero, one and two; wherein R² is selected from the group consisting of hydrido and alkyl; wherein R³ is selected from the group consisting of hydrido, cycloalkylalkyl, aralkyl and haloaralkyl; wherein each of R⁴ and R⁶ is independently selected from the group consisting of hydrido and methyl; wherein R⁵ is propargyl or a propargyl-containing moiety; wherein R⁷ is selected from the group consisting of alkyl, cycloalkylalkyl and aralkyl; wherein R⁸ is selected from the group consisting of hydrido, alkyl, hydroxyalkyl, cycloalkyl, cycloalkylalkyl, alkenyl and haloalkenyl; and wherein any one of said R¹ through R⁸ groups having a substitutable position may be substituted with one or more groups selected from alkyl, hydroxy, alkoxy and alkenyl.

19. The method of claim 18 wherein R¹ is selected from the group consisting of alkyl, trifluoromethyl, cycloalkyl, cycloalkylalkyl, phenyl, halophenyl, phenylalkyl, halophenylalkyl, naphthyl, halonaphthyl, naphthylalkyl and halonaphthylalkyl; wherein x is a number selected from the group consisting of zero, one and two; wherein R² is selected from the group consisting of hydrido and alkyl; wherein R³ is selected from the group consisting of hydrido, cycloalkylalkyl, phenylalkyl, halophenylalkyl, naphthylalkyl and halonaphthylalkyl; wherein each of R⁴ and R⁶ is independently selected from the group consisting of hydrido and methyl; wherein R⁵ is propargyl or a propargyl-containing moiety; wherein R⁷ is selected from the group consisting of cyclohexylmethyl and benzyl, either one of which may be substituted with one or more groups selected from the group consisting of alkyl, hydroxy and alkoxy; and wherein R⁸ is selected from the group consisting of hydrido, alkyl, cycloalkyl, cycloalkylalkyl, hydroxyalkyl, alkenyl and haloalkenyl.

20. The method of claim 19 wherein R¹ is selected from the group consisting of methyl, ethyl, n-propyl, isopropyl, n-butyl, isobutyl, sec-butyl, tert-butyl, trifluoromethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is a number selected from the group consisting of zero, one and two; wherein R² is selected from the group consisting of hydrido, methyl, ethyl and n-propyl; wherein R³ is selected from the group consisting of hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of R⁴ and R⁶ is independently selected from the group consisting of hydrido and methyl; wherein R⁵ is propargyl or a propargyl-containing moiety; wherein R⁷ is cyclohexylmethyl; and wherein R⁸ is selected from the group consisting of methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl.

21. The method of claim 20 wherein R¹ is selected from the group consisting of methyl, ethyl, n-propyl, isopropyl, benzyl, phenethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is zero or two; wherein R² is selected from the group consisting of hydrido, methyl, ethyl and n-propyl; wherein R³ is selected from the group consisting of hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of R⁴ and R⁶ is hydrido; wherein R⁵ is propargyl or a propargyl-containing moiety; wherein R⁷ is cyclohexylmethyl; and wherein R⁸ is selected from the group consisting of ethyl, n-propyl, n-butyl, isobutyl, cyclopropyl, cyclobutyl, cyclopropylmethyl, allyl and vinyl.

22. The method of claim 21 wherein said compound is selected from compounds of Formula II

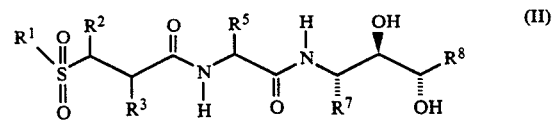

wherein R¹ is selected from the group consisting of isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaphthylmethyl and chloronaphthylmethyl; wherein R² is selected from the group consisting of hydrido, methyl, ethyl and phenyl; wherein R³ is selected from the group consisting of hydrido, cyclohexylmethyl, benzyl, fluorobenzyl, chlorobenzyl, fluoronaphthylmethyl and chloronaphthylmethyl; wherein each of R⁴ and R⁶ is hydrido; wherein R⁵ is propargyl or a propargyl-containing moiety; wherein R⁷ is cyclohexylmethyl; and wherein R⁸ is selected from the group consisting of n-propyl, isobutyl, cyclopropyl, cyclopropylmethyl, allyl and vinyl.

23. The method of claim 22 wherein said compound is N-[[1R*-[[1S,1R*-(cyclohexylmethyl)-2S*,3R*-dihydroxy-5-methylhexyl]amino]carbonyl]-3-butynyl]-α-[[(1,1-dimethylethyl)sulfonyl]methyl]benzenepropanamide.

24. The method of claim 22 wherein said compound is N-[[1R*-[[1S,1R*-(cyclohexylmethyl)-2S*,3R*-dihydroxy-5-methylhexyl]amino]carbonyl]-3-butynyl]-αR*-[[(1,1-dimethylethyl)sulfonyl]methyl]benzenepropanamide.

25. The method of claim 22 wherein said compound is N-[1S,1R*-(cyclohexylmethyl)-2S*,3R*-dihydroxy-5-methylhexyl]-2R*-[[1-oxo-3-(phenylsulfonyl)propyl]amino]-4-pentynamide.

* * * * *